(12) United States Patent
Hairston et al.

(10) Patent No.: US 7,576,844 B2
(45) Date of Patent: Aug. 18, 2009

(54) SYSTEMS AND METHODS FOR USE IN DETECTING HARMFUL AEROSOL PARTICLES

(75) Inventors: Peter P. Hairston, Severna Park, MD (US); Carl B. Freidhoff, New Freedom, PA (US)

(73) Assignee: Northrop Grumman Corporation, Los Angeles, CA (US)

( * ) Notice: Subject to any disclaimer, the term of this patent is extended or adjusted under 35 U.S.C. 154(b) by 85 days.

(21) Appl. No.: 11/349,340

(22) Filed: Feb. 8, 2006

(65) Prior Publication Data
US 2006/0232775 A1    Oct. 19, 2006

Related U.S. Application Data

(60) Provisional application No. 60/650,521, filed on Feb. 8, 2005.

(51) Int. Cl.
*G01N 21/00* (2006.01)
(52) U.S. Cl. .................... 356/73; 356/417; 356/337
(58) Field of Classification Search ............. 356/246, 356/417, 337, 72–73
See application file for complete search history.

(56) References Cited

U.S. PATENT DOCUMENTS

| | | | |
|---|---|---|---|
| 4,164,373 A | 8/1979 | Schuss | |
| 4,405,199 A | 9/1983 | Ogle | |
| 4,573,796 A * | 3/1986 | Martin et al. | 356/318 |
| 4,657,398 A | 4/1987 | Brunsting | |
| 5,288,995 A | 2/1994 | Stracher | |
| 5,474,910 A | 12/1995 | Alfano | |
| 5,528,045 A * | 6/1996 | Hoffman et al. | 250/458.1 |
| 5,561,515 A | 10/1996 | Hairston et al. | |
| 5,681,752 A | 10/1997 | Prather | |
| 5,698,397 A * | 12/1997 | Zarling et al. | 435/6 |
| 5,701,012 A | 12/1997 | Ho | |
| 5,751,429 A | 5/1998 | Wada et al. | |
| 5,760,900 A * | 6/1998 | Ito et al. | 356/338 |
| 5,828,452 A | 10/1998 | Gillispie | |
| 5,895,922 A | 4/1999 | Ho | |
| 5,999,250 A | 12/1999 | Hairston et al. | |
| 6,249,341 B1 * | 6/2001 | Basiji et al. | 356/73 |
| 6,266,139 B1 * | 7/2001 | Mannhardt | 356/246 |
| 6,473,176 B2 * | 10/2002 | Basiji et al. | 356/326 |
| 6,532,067 B1 | 3/2003 | Chang et al. | |
| 6,592,822 B1 * | 7/2003 | Chandler | 422/82.05 |
| 6,671,044 B2 | 12/2003 | Ortyn et al. | |
| 6,787,104 B1 | 9/2004 | Mariella, Jr. | |
| 6,831,279 B2 | 12/2004 | Ho | |
| 7,015,484 B2 | 3/2006 | Gillispie | |
| 7,064,827 B2 * | 6/2006 | Nurmikko et al. | 356/338 |
| 7,106,442 B2 * | 9/2006 | Silcott et al. | 356/338 |

(Continued)

OTHER PUBLICATIONS

Arndt-Jovin, D.J.; Grimwade, B.G.; Jovin, T.M.; "A Dual Laser Flow Sorter Utilizing a CW Pumped Dye Laser", 1980, Cytometry, vol. 1, No. 2.*

(Continued)

*Primary Examiner*—Kara E Geisel
(74) *Attorney, Agent, or Firm*—Rothwell, Figg, Ernst & Manbeck, P.C.

(57) ABSTRACT

The invention provides systems and methods for detecting aerosols. The systems and methods can be used to detect harmful aerosols, such as, bio-aerosols.

19 Claims, 8 Drawing Sheets

U.S. PATENT DOCUMENTS

| | | | |
|---|---|---|---|
| 7,116,407 B2 * | 10/2006 | Hansen et al. | 356/73 |
| 7,123,416 B1 | 10/2006 | Erdogan et al. | |
| 2002/0030812 A1 * | 3/2002 | Ortyn et al. | 356/326 |
| 2002/0093641 A1 * | 7/2002 | Ortyn et al. | 356/28 |
| 2002/0094116 A1 * | 7/2002 | Frost et al. | 382/129 |
| 2002/0094166 A1 | 7/2002 | Weerden et al. | |
| 2003/0235919 A1 * | 12/2003 | Chandler | 436/43 |
| 2004/0007675 A1 * | 1/2004 | Gillispie et al. | 250/458.1 |
| 2004/0057050 A1 | 3/2004 | Beck et al. | |
| 2004/0223135 A1 * | 11/2004 | Ortyn et al. | 356/28 |
| 2005/0036139 A1 * | 2/2005 | Johnson | 356/246 |
| 2005/0073683 A1 | 4/2005 | Gard et al. | |
| 2005/0105077 A1 * | 5/2005 | Padmanabhan et al. | 356/39 |
| 2005/0162648 A1 | 7/2005 | Auer et al. | |
| 2005/0255456 A1 | 11/2005 | Murray et al. | |
| 2006/0238757 A1 * | 10/2006 | Silcott | 356/338 |

OTHER PUBLICATIONS

Define:emit—Google Search, retrieved Nov. 27, 2007, www.google.com.*

Office Action from U.S. Appl. No. 11/349,341, dated Jun. 15, 2007, 16 pages.

Office Action from U.S. Appl. No. 11/349,344 dated Jun. 15, 2007, 17 pages.

International Search Report and Written Opinion issued in PCT/US06/04279 on Sep. 26, 2007, 16 pp.

Fellner-Feldegg, "Dual Laser Flow Cytometry: Focal Length Compensation When Focussing Through a Single Lens", Cytometry 6, 1985, pp. 286-289.

Definitions of "microbe" on the Web, search of Dec. 13, 2007, 2 pages.

Definitions of "count" on the Web, search of Nov. 28, 2007, 3 pages.

Office Action issued in U.S. Appl. No. 11/349,341 on Dec. 17, 2007, 21 pages.

Office Action issued in U.S. Appl. No. 11/349,344 on Jan. 2, 2008, 18 pages.

Office Action issued in U.S. Appl. No. 11/755,535 on Dec. 18, 2007, 20 pages.

* cited by examiner

SYSTEMS AND METHODS FOR USE IN DETECTING HARMFUL AEROSOL PARTICLES

This application claims the benefit of U.S. Provisional Patent Application No. 60/650,521, filed on Feb. 8, 2005. The entire content of the above referenced provisional application is incorporated herein.

This application is related to U.S. patent application Ser. No. 11/349,341, filed on Feb. 8, 2006 and to U.S. patent application Ser. No. 11/349,344, now U.S. Pat. No. 7,423,751, filed on Feb. 8, 2006.

BACKGROUND OF THE INVENTION

1. Field of the Invention

The invention generally relates to systems and methods for, inter alia, detecting harmful aerosol particles, and, in some embodiments, to multi-spectral aerosol particle measurement systems.

2. Discussion of the Background

Aerosol particles (or aerosols) are particles that are suspended in a gas (e.g., the air we breathe). Some aerosol particles may be harmful to humans. Thus, there is a need to detect the presence of harmful aerosol particles in an area in which humans are present.

SUMMARY OF THE INVENTION

The present invention provides systems and methods for, among other things, detecting the presence of harmful or other aerosol particles, such as, for example, biological aerosols.

A detector system according to one embodiment of the invention includes: a first emitter (e.g., a laser or light emitting diode) configured to emit first excitation energy into a first region of space such that a particle located within the first region of space may be exposed to the first excitation energy; a second emitter configured to emit second excitation energy into a second region of space such that when the particle is located within the second region of space the particle may be exposed to the second excitation energy, wherein the system is configured such that, after the particle passes through the first region, the particle will likely pass through the second region; an emission detector (e.g., a photomultiplier) having a detector input; a first filter disposed in front of a first portion of the detector input; a second filter disposed in front of a second portion of the detector input; and one or more optical elements being configured such that (a) when a particle is located at a position within the first region and exposed to the first excitation energy and produces a first emission, the first emission is directed such that the first emission passes through the first filter but not the second filter prior to reaching the detector input, and (b) when the particle is located at a position within the second region and exposed to the second excitation energy and produces a second emission, the second emission is directed such that the second emission passes through the second filter but not the first filter prior to reaching the detector input.

The system may also include a particle detector and an emitter controller. The particle detector may be configured to detect whether a particle is within the first region of space or about to enter the first region of space, and the emitter controller may be configured to cause the first emitter to emit radiation in response to the particle detector detecting that a particle is within the first region of space or about to enter the first region of space.

The system may also include a third emitter configured to emit third excitation energy into a third region of space such that when the particle is located within the third region of space the particle may be exposed to the third excitation energy, wherein the system is configured such that, after the particle passes through the second region, the particle will likely pass through the third region. The wavelength or wavelengths of the first excitation energy may be between about 250 nanometers and 300 nanometers, and the wavelength or wavelengths of the second excitation energy may be between about 310 nanometers and 370 nanometers.

A detection method according one embodiment of the invention includes the steps of: (a) obtaining or making a detector system comprising: a first emitter configured to emit first excitation energy into a first region of space; a second emitter configured to emit second excitation energy into a second region of space; an emission detector having a detector input; a first filter disposed in front of a first portion of the detector input; and a second filter disposed in front of a second portion of the detector input; (b) using the first emitter to emit the first excitation energy into the first region; (c) using the second emitter to emit the second excitation energy into the second region; (d) receiving a fluid containing a particle; (e) directing the fluid so that the particle is first exposed primarily to the first excitation energy first and then, at a later time, exposed primarily to the second excitation energy; (f) when the particle is exposed to the first excitation energy and, as a result of the exposure, produces radiation, directing at least some of the radiation to the first filter, but directing at most only an insubstantial amount of the radiation to the second filter; and (g) when the particle is exposed to the second excitation energy and, as a result of the exposure, produces radiation, directing at least some of the radiation to the second filter, but directing at most only an insubstantial amount of the radiation to the first filter.

The wavelength or wavelengths of the first excitation energy may be between about 250 nanometers and 300 nanometers, and the wavelength or wavelengths of the second excitation energy are between about 310 nanometers and 370 nanometers.

The method may also include the steps of: detecting whether a particle is within the first region of space or about to enter the first region of space and causing the first emitter to emit radiation in response to detecting that a particle is within the first region of space or about to enter the first region of space.

The method may also include the step of distinguishing particles of a given composition type from other particles of other composition types based on comparisons of data generated by the detector to data generated from prior assays of particles of the given composition type.

A detection method according to another embodiment includes the steps of: using a first emitter to emit into a region of space first radiation having a first wavelength; while using the first emitter to emit into the region the first radiation, using a second emitter to emit into the region second radiation having a second wavelength, so that, when a particle transits through the region of space, the particle is simultaneously exposed to the first and second radiation and, in response to being exposed to the radiation, produces elastic and/or inelastic radiation; modulating the intensity of the first radiation at a first frequency and modulating the intensity of the second radiation at a second frequency; transmitting, by reflective or refractive optics, the elastic and inelastic radiation to the detector through a filter or a combination of filters; receiving an output signal from the detector; and determining (e.g., using Fourier analysis or frequency down-mixing) the intensity of the produced elastic and/or inelastic radiation that can attributed to the first emitter and the intensity of the produced elastic and/or inelastic radiation that can attributed to the second emitter.

The method may also include the step of, in response to detecting the particle is within the region of space or about to enter the region of space, causing each of the two emitters to emit the first and second radiation, respectively, while the particle transits through the region.

In some embodiments, the first emitter is configured to emit radiation in a first direction, the second emitter is configured to emit radiation in a second direction that intersects the first direction, and an emitter reflector is disposed at the intersection of the first direction and the second direction, wherein the emitter reflector is configured to pass the first radiation in the first direction and reflect the second radiation in the first direction.

A detector system according to another embodiment includes: a first intensity-modulated emitter configured to emit intensity-modulated first radiation into a region of space; a second intensity-modulated emitter configured to emit intensity-modulated second radiation into the region of space, such that, when a particle transits through the region of space, the particle is simultaneously exposed to the radiation from the first and second emitters and, in response to being exposed to the radiation, produces elastic and/or inelastic radiation; a detector; reflective or refractive optics configured to transmit the elastic and/or inelastic radiation to the detector; a processor configured to determine by spectral analysis the intensity of the produced elastic and/or inelastic radiation that can attributed to the first radiation and the intensity of the produced elastic and/or inelastic radiation that can attributed to the second radiation.

The above and other features and advantages of the present invention, as well as the structure and operation of preferred embodiments of the present invention, are described in detail below with reference to the accompanying drawings.

BRIEF DESCRIPTION OF THE DRAWINGS

The accompanying drawings, which are incorporated herein and form part of the specification, help illustrate various embodiments of the present invention and, together with the description, further serve to explain the principles of the invention and to enable a person skilled in the pertinent art to make and use embodiments of the invention. In the drawings, like reference numbers indicate identical or functionally similar elements.

DETAILED DESCRIPTION OF PREFERRED EMBODIMENTS

Figure 1:
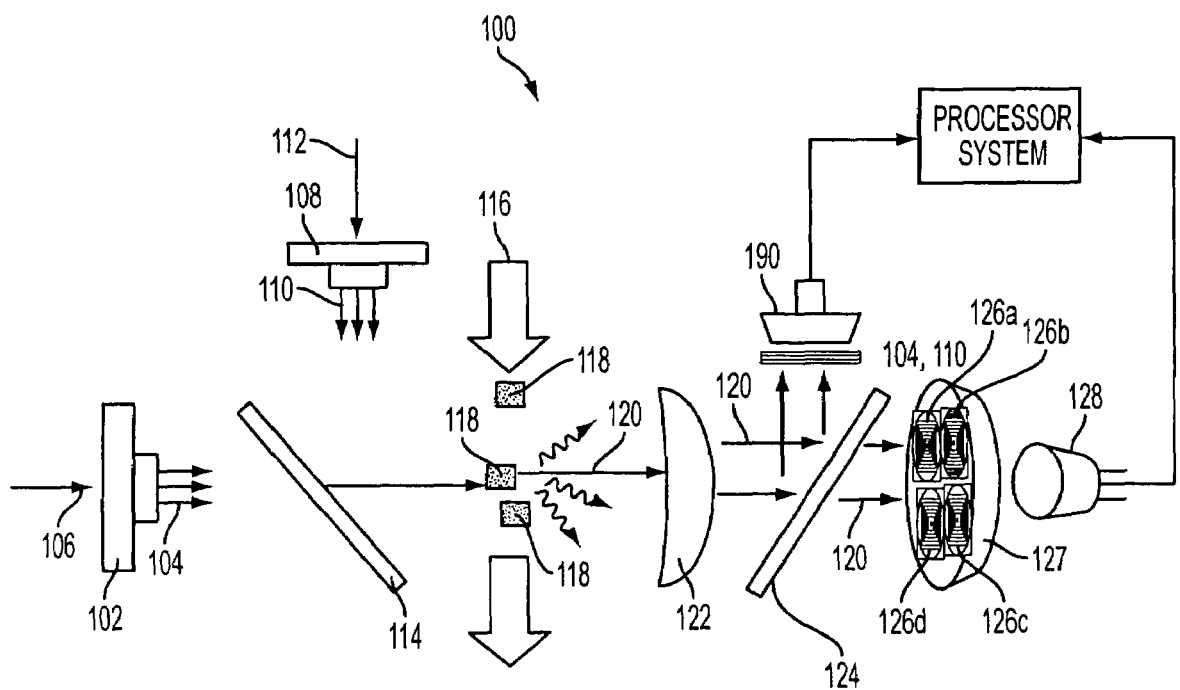
FIG. 1 is a schematic of a system according to a first embodiment of the invention.

As used herein, the term "a" means "one or more," unless expressly noted otherwise.

One widely accepted method of discriminating particles of biological nature in nearly real time is through measurement of intrinsic fluorescence of airborne particles. Using this method, potential biological threat agents, such as anthrax or drug content within inert carrier materials from a nebulizer, may be distinguished from benign "background" particles normally present in ambient air.

Biological threat particles such as bacteria, toxins, and viruses contain a variety of fluorophores that can be used to discriminate or characterize the particles. The primary fluorophores include tryptophan, NADH, flavins, dipicolinic acid, phenylalanine, tyrosine, and other proteins. In addition, residues from the production of biological threat particles can indicate the manufacture of biological threats. Examples of these residues are growth media and bacteria used as hosts for bacterial phage viruses.

Fluorophores have characteristic excitation and emission spectra. The emission spectra generally span several tens or hundreds of nanometers of wavelength, and may overlap. Background particles that are not of interest for a specific detection requirement may have fluorescence characteristics of their own.

The fluorescence characteristics of the background particles may be similar to some, but usually not all, of that of the fluorophores in particles that are of interest as targets for detection. The fluorescence of the fluorophores targeted for detection may thus overlap that of the background particles.

Background particles may also have additional fluorescence properties that are distinct from that of the target particles. Fluorescence measurements that are indicative of background particles may also be useful in discriminating background particles from particles that are targets for detection.

Aerosol particle fluorescence measurements are typically performed on a continuous basis. In an aerosol particle fluorescence measurement, radiation of various wavelengths is directed at a flowing fluid that contains particles, causing the particles to produce fluorescent radiation at wavelengths that are characteristic of the particles. Measurement of individual particles, as opposed to aggregates of particles, provides better discrimination of target particles in a background, since each individual measurement is made on either a target particle or a background particle without commingling of the measurements.

Aerosol fluorescence measurements do not typically incur any operating costs other than the electrical power necessary to run an emitter, a detector, and control circuitry. Aerosol particle fluorescence measurements are thus often used to indicate the possibility of threat particles.

In this way, aerosol fluorescence measurements can be used as an initial fast screening tool. If the aerosol particle fluorescence measurement gives a positive indication of a threat, it may be followed by slower, more costly measurements to confirm or refute the initial threat indication.

Since there are multiple biological and background particle fluorophores, more specific indicators of biological threats or other fluorescent characteristics of particles may be necessary. Fluorescence measurements can be made more specific by increasing the number excitation and emission wavelength regions that are used.

When multiple excitation wavelengths are used, various wavelengths may be sequenced in time, or separated in space, or both. Separating excitation wavelengths in time or space avoids confounding emissions stemming from one excitation with emissions stemming from a different excitation.

Additional specificity for the classification of fluorescent particles can be gained by measurement of light scatter or aerodynamic particle size along with the fluorescence measurements.

The fluorescence emitted by a single particle or from a volume of aerosol may be of low intensity. If the fluorescence is distributed among too many emission detection channels, the amount of detectable fluorescent light (or number of photons) per channel may provide an insufficient per-channel signal-to-noise ratio. If the signal-to-noise ratio of a channel is small, it may be difficult to provide a useful correlation among signals detected from identical input particles.

A system that measures multiple emissions, including multiple emissions from multiple excitation wavelengths, may be expensive and complex. Such a system may require a separate detector for each emission wavelength region.

Photomultiplier tube detectors costing hundreds of dollars are typically necessary for the low optical signal levels typical of biological aerosol particles. While multi-element detectors such as multi-channel plates, image enhanced CCDs, and multi-segment photomultipliers could also be used, these are all relatively expensive when suited to the needed sensitivity and bandwidth.

If a single detector were used, the cost and complexity associated with multiple detectors could be avoided. At least some embodiments described herein reduce the cost and complexity of particle characterization systems by using only a single detector to detect multiple wavelength bands of fluorescence emissions from a particle or aerosol, or, more generally, they use a number of detectors that is fewer than the number of wavelength channels detected.

It should be noted that these methods may be applied to other fluorescence measurement applications, such as for particles in any fluid, with hydrosols in a flow cytometer being one example. Further, these concepts may also be applicable to other excitation emission wavelength based optical measurements, such as measuring Raman emissions and laser-induced breakdown emissions.

In a system with multiple detectors, it is possible to detect multiple fluorescence channels simultaneously. A system with multiple detectors may thus acquire a complete set of emission spectral information from a single particle.

A single detector system, on the other hand, obtains a single wavelength or color band from any given particle measurement. For applications such as detection of biological threat aerosols, however, the aerosol cloud will be present for several seconds or more. Thus, particles measurements may be taken serially over a selection of color band settings within the time that the aerosol cloud is present. The fluorescence characteristics that are then measured will provide more complete information about the particles within the cloud and enhance discrimination of particle types.

FIG. 1 is a schematic of a multi-spectral aerosol particle measurement system 100 according to a first embodiment of the invention. As shown in FIG. 1, a multi-spectral aerosol particle measurement system 100 may include a long emitter 102 emitting long wavelength radiation 104 (e.g., UV light at approximately 340 nm) in a first direction 106 and a short emitter 108 emitting short wavelength radiation 110 (e.g., UV light at approximately 280 nm) in a second direction 112 (direction 112 may be orthogonal to direction 106 as illustrated in FIG. 1).

An emitter reflector 114 may be positioned at an intersection of first direction 106 and second direction 112 to pass long wavelength radiation 104 in first direction 106 and reflect short wavelength radiation 110 in first direction 106. In one embodiment, emitter reflector 114 is a filter, such as a dichroic filter, that is transparent to long wavelength radiation 104 and reflective to short wavelength radiation 110. In another embodiment, emitter reflector 114 comprises a plurality of filters that can be used sequentially to produce various bands of long wavelength radiation 104 and short wavelength radiation 110.

A flowing fluid 116 that contains particles may intersect first direction 106 such that the particles in fluid 116 (or "particle stream 116") are sequentially exposed to both long wavelength radiation 104 and short wavelength radiation 110. A particle 118 in particle stream 116 intersecting first direction 106 may produce elastic and inelastic emission wavelengths (the inelastic emission wavelengths may include a fluorescent radiation 120 resulting from the particle's exposure to either the long wavelength radiation or the short wavelength radiation, sequentially, or both) when exposed to the long or short wavelength radiation 104, 110.

A collimating lens 122 positioned in first direction 106 may receive and collimate long and short wavelength radiation 104, 110 and fluorescent radiation 120. A detector reflector 124 (e.g., a dichroic filter or the like) positioned in first direction 106 may reflect short wavelength radiation and pass fluorescent radiation 120 so that it passes through at least one a plurality of detector filters 126a-d. Each of detector filters 126a-d may be placed in the optical detection path of a detector 128.

In one embodiment, detector filters 126a-d may be disposed in a holder 127. Holder 127 may be mechanically moved (e.g., rotated) in a controlled manner to position different detector filters 126a-d in the optical path of detector 128. The sequencing of detector filters 126a-d may be combined with the sequencing of two, as shown, or more excitation sources.

In one embodiment, filter 124 reflects light having a wavelength shorter than 300 nm so that elastic scatter caused by a particle exposed to, for example, a 280 nm radiation source is detected by light scatter detector 190, and it's amplitude measured by the a data processor (e.g., a signal processor or other data processor). Further, filter 126A is configured to pass 400-500 nm fluorescence from the particle exposed to a 340 nm light, while filter B is configured to pass 320-400 nm fluorescence from the particle when it is exposed to 280 nm light.

After measuring at least one particle, but typically after measuring a number of particles greater than 100, or after measuring particles for a fixed time interval (e.g., 1 second), filter holder 127 is moved (e.g., rotated) to a second position, such that 500-600 nm fluorescence is measured when a particle is in the 340 nm light, and 400-500 nm fluorescence is measured when the particle is in the 280 nm light. An example sequence of operation is summarized as: Filter setting 1 measurements: 280 nm light scatter, 400-500 nm fluorescence from 340 nm source, 300-400 nm fluorescence from 280 nm source; Filter setting 2 measurements: 280 nm light scatter, 500-600 nm fluorescence from 340 nm source, 400-500 nm fluorescence from 280 nm source.

In one embodiment, long emitter 102 and short emitter 108 may be paired with each detector filters 126a-d in turn to detect various fluorophores. In one embodiment, a controller (e.g., a computer or other control system) may be used to switch long emitter 102 and short emitter 108 on and off while each of four detector filters 126a-d are positioned in first direction 106.

A fluorescence emission band of interest excited by short emitter 108 may partly correspond to wavelength 104 of long emitter 102. In this embodiment, light scatter from long emitter 102, rather than fluorescent radiation 120, can be measured at one of the detector filter 126 sequence settings.

In general it is advantageous to obtain a scattered light intensity simultaneously with, or corresponding to, each fluorescence measurement. This allows particles to be differentiated based on their fluorescence to light scatter ratios. Fluorescence to light scatter ratios may be indicative of the concentration or quantum efficiency of the fluorophores in particle stream 116.

In an alternative embodiment, it could be advantageous to include more than one filter at each of detector filters 126a-d. In this embodiment, the combined response of two filters, such a long pass filter combined with a short pass filter, could be used to create a band pass filter.

In another embodiment, a filter 126 may include or consist of a diffraction grating or a prism. In this embodiment, the diffraction grating or prism could be tilted sequentially to deliver a different portion of the spectrum to detector 128.

In another embodiment, a filter 126 may include or consist of an electrically or acoustically tunable filter, such as a MEMS based device. The optical and mechanical configuration of such tunable filters can be arranged to provide sequentially any selected wavelength regions of the collected emission to detector 128.

Figure 2:
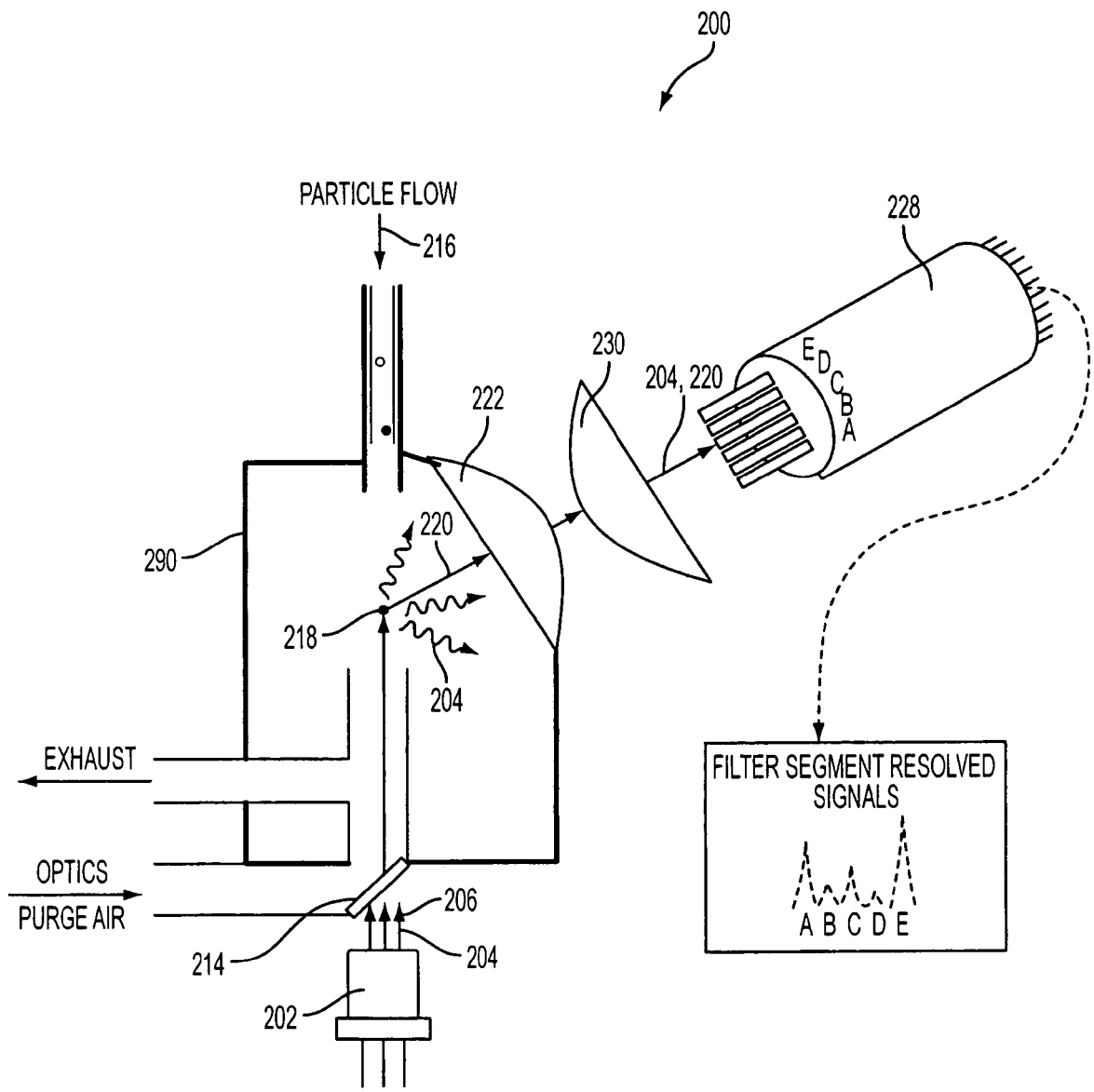
FIG. 2 is a schematic of a system according to a second embodiment of the invention.

FIG. 2 is a schematic of a multi-spectral aerosol particle measurement system 200 according to a second embodiment of the invention. As shown in FIG. 2, multi-spectral aerosol particle measurement system 200 may include a long emitter 202 emitting in a first direction 206 long wavelength radiation 204 (e.g., light having a wavelength of about 375 nm). A window 214, kept clean by a filtered purge air flow, allows radiation 204 to enter an optical chamber 290.

A fluid flow 216 containing particles ("particle stream 216") may traverse first direction in a direction substantially opposite to that of long wavelength radiation 204. A particle 218 in stream 216 may produce fluorescent radiation 220 when exposed to radiation 204. An optical apparatus, which may include a collimating lens 222 and a focusing lens 230, may be positioned to receive and collimate fluorescent radiation 220, as well as long wavelength radiation 204 that has been scattered.

The focusing lens 230 may be positioned to receive and focus collimated radiation 204 and fluorescent radiation 220. A detector 228 may be placed at a focus of focusing lens 230 to receive elastic scatter and fluorescent radiation 220. Accordingly, the optical apparatus may be configured to direct the radiation 220 and scatter to the detector.

In one embodiment, detector 228 may be a photomultiplier tube with a sufficiently large photosensitive area for there to be multiple filters A, B, C, D, and E positioned in front of detector 228. In one embodiment, it may be advantageous for signal separation to have opaque strip separating each filter A, B, C, D, and E.

In several embodiments (including similar alternative embodiments), collimating lens 222 and focusing lens 230 may be reflective or refractive optics (e.g., spherical, ellipsoidal, or parabolic reflectors). In several embodiments, an optical fiber or a light pipe may be used to transmit long wavelength radiation 204 to particle stream 216.

In this embodiment, measurements may be obtained from multiple wavebands of fluorescent radiation 220 produced by a single particle 218. In this embodiment, fluorescent radiation 220 produced by single particle 218 is directed or "imaged" onto array of filters A, B, C, D, and E of detector 228 as particle 218 moves in particle stream 216. In a preferred embodiment, the array of filters together covers the range of fluorescence and light scatter produced by target particles and background particles to be differentiated. For 375 nm excitation, a preferred series of filters is: A=550-600 nm, B=500-550 nm, C=450-500 nm, D=400-450 nm, E=<400 nm, with E including elastically scattered light. In this embodiment, fluorescent radiation 220 produced by single particle 218 is directed or imaged sequentially through each of filters A, B, C, D, and E. This is illustrated in FIG. 8.

Figure 8:
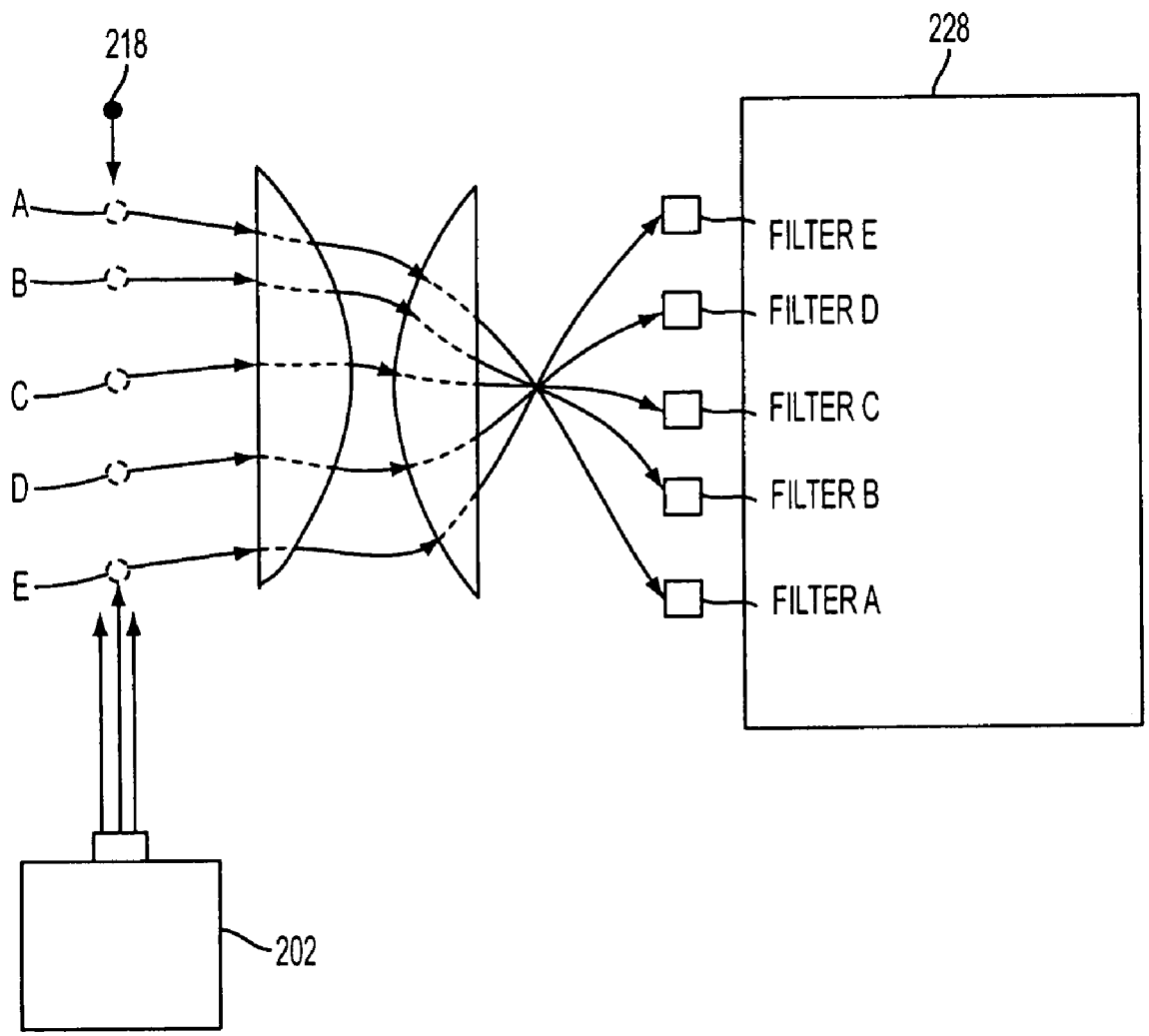
FIG. 8 illustrates a particle moving from a point A to a point E through points B-D.

FIG. 8 illustrates particle 218 moving from point A to point E through points B-D. When particle 218 is located at or near point A, the elastic and inelastic emission wavelengths produced by particle 218, which emission wavelengths are produced as a result of particle 218 receiving radiation 204, pass only or primarily through a single filter (e.g., filter A). Similarly, at a later point in time, when particle 218 is located at or near point B, the emission wavelengths produced by particle 218 pass only or primarily through a single filter (e.g., filter B). Likewise, at a still later point in time, when particle 218 is located at or near point C, D or E, the emission wavelengths produced by particle 218 pass only or primarily through a single filter (e.g., filter C, D or E, respectively). Thus, in this manner, fluorescent radiation 220 produced by single particle 218 may be directed or imaged sequentially through each of filters A, B, C, D, and E.

As illustrated in FIG. 8, by employing two or more filters between the particle and a single detector, it is possible to use only a single detector to detect elastic and multiple inelastic emission wavelengths from an individual particle that, while moving from one point to another, is exposed to an excitation wavelength. In several embodiments, multi-element photomultipliers, micro channel plates, or image enhanced charge coupled devices (CCD's) could also accomplish multispectral sensing. In other words, embodiments of the present invention enable one to create a detection system wherein the number of detectors is less than the number of emission wavelengths detected. This is advantageous because, typically, the most costly components of a detection system are the detectors themselves.

Figure 3:
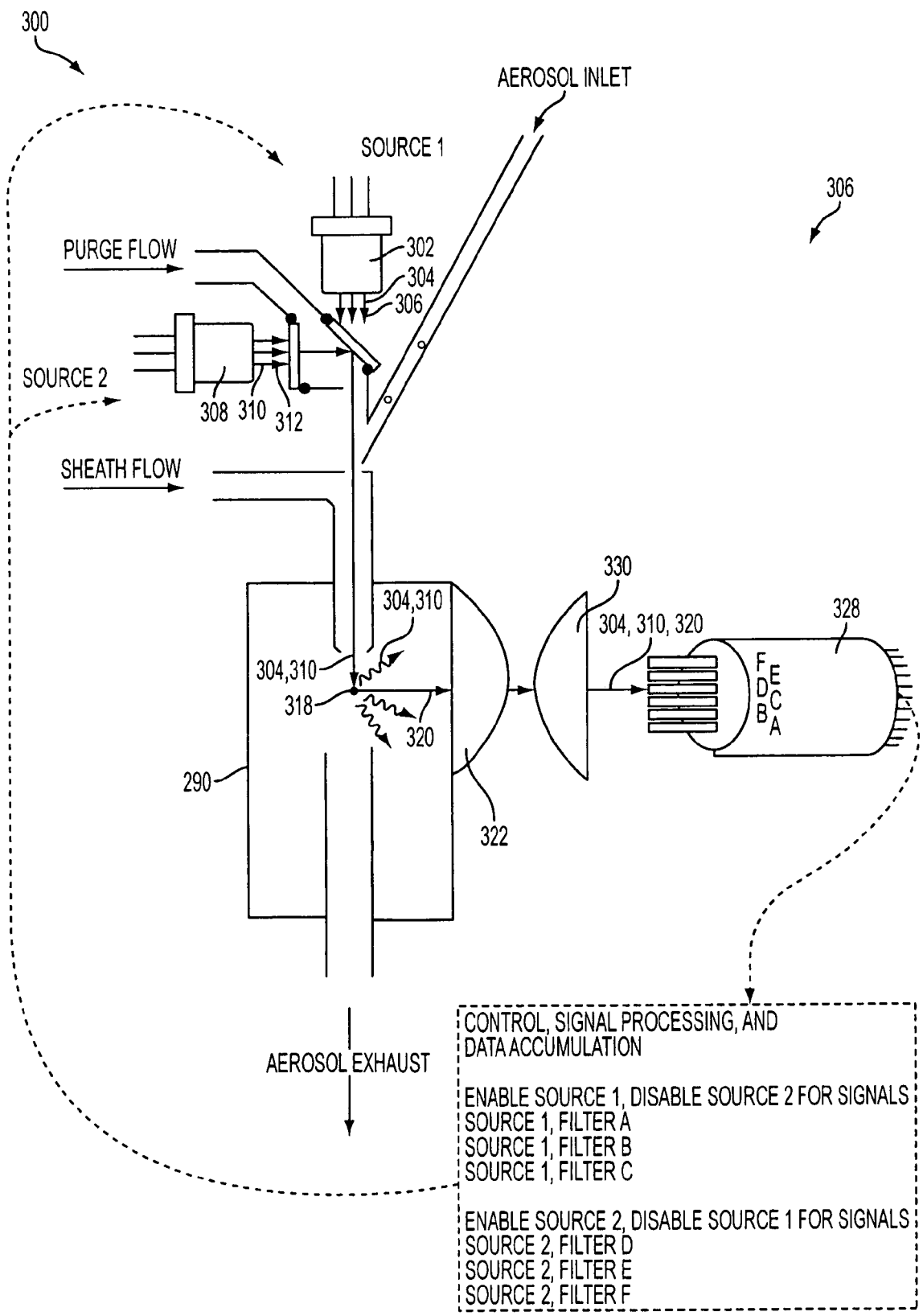
FIG. 3 is a schematic of a system according to a third embodiment of the invention.

FIG. 3 is a schematic of a multi-spectral aerosol particle measurement system 300 according to a third embodiment of the invention. As shown in FIG. 3, multi-spectral aerosol particle measurement system 300 may include a long emitter 302 emitting in a first direction 306 long wavelength radiation 304 (e.g., light having a wavelength of about 405 nm) and a short emitter 308 emitting in a second direction 312 short wavelength radiation 310 (e.g., light having a wavelength of about 280 nm).

An emitter reflector 314 (e.g., a dichroic mirror) may be placed at an intersection of first direction 306 and second direction 312 to pass long wavelength radiation 304 in first direction 306 and reflect short wavelength radiation 310 in first direction 306. In one embodiment, emitter reflector 314 comprises a plurality of filters (not shown) that can be used to produce three or more different wavelength bands of radiation. Reflector 314 may be the same as reflector 124 described above.

A particle 318 in a fluid flow may travel along first direction 306 such that particle traverses along in the locations of both long wavelength radiation 304 and short wavelength radiation 310. The particle 318 may produce radiation at a fluorescent wavelength radiation 320 when exposed to long or short wavelength radiation 304, 310.

A collimating lens 322 may be positioned to receive and collimate fluorescent radiation 320 as well as scattered long and short wavelength radiation 304, 310. A focusing lens 330 may be positioned to receive and focus collimated long or short wavelength radiation 304, 310 and fluorescent radiation 320.

A detector 328 may be positioned at a focus of focusing lens 330 to receive long or short wavelength radiation 304, 310 and fluorescent radiation 320. In one embodiment, detector 328 may be a photomultiplier tube with a sufficiently large photosensitive area for there to be multiple filters A, B, C, D, E and F positioned in front of detector 328.

In some embodiments, collimating lens 322 and focusing lens 330 may be reflective or refractive optics (e.g., spherical, ellipsoidal, or parabolic reflectors). In some embodiments, an optical fiber or a light pipe may be used to transmit long and short wavelength radiation 304 and 310.

In this embodiment, long and short wavelength radiation 304, 310 are different but overlapped spatially, and are switched on for alternate time intervals.

For example, long emitter 302 would emit into a predefined region of space and for a first time interval long wavelength radiation 304, during which time interval the particle 318 moves through at least a first portion of the region of space in which the radiation 304 is present, thereby exposing the particle to the radiation 304. As the particle 318 moves through the first portion of the region, emissions caused by the particle's exposure to the radiation may be produced. These emissions may be sequentially approximately focused onto filters A, B and then C.

After the first time interval and while the particle 318 is still located within the region, long emitter 302 ceases emitting radiation 304 and short emitter 308 would be switched on to emit short wavelength radiation 310 into the region for a second time interval, during which second time interval the particle 318 moves through at least a second portion of the region of space in which the radiation 310 is present, thereby exposing the particle to radiation 310. As the particle 318 moves through the second portion of the region, emissions caused by the particle's exposure to radiation 310 may be produced. These emissions may be sequentially approximately focused onto filters D, E and then F.

For 405 and 280 nm emitters, one preferred selection of filters is: A=<420 nm with partial attenuation of 405 nm such that the scattered 405 nm light can be measured at the same detector gain as the weaker fluorescence signals excited by 405 nm; B=430-500 nm (fluorescence excited by 405 nm); C=500-600 nm (fluorescence excited by 405 nm); D=310-380 nm (fluorescence excited by 280 nm); E=430-500 nm (fluorescence excited by 280 nm); F=<300 nm with partial attenuation of 280 nm such that the scattered 280 nm light is can be measured at the same detector gain as the weaker fluorescence signals excited by 280 nm.

FIG. 3, and also FIG. 2 for that matter, show radiation 204, 304 and 310 being emitted along direction 206, 306, respectively, which is the opposite direction in which the fluid containing particle 218, 318 flows. This may provide approximately uniform illumination of particle 218, 318 as it flows through the excitation region. This may further allow sub-regions of the fluid to be imaged easily to detector filter array A, B, C, D, E, and F. However, the concept of using a sequentially positioned filter array A, B, C, D, E, and F may be applied regardless of the direction from which the excitation radiation arrive at the fluid flow.

Figure 4:
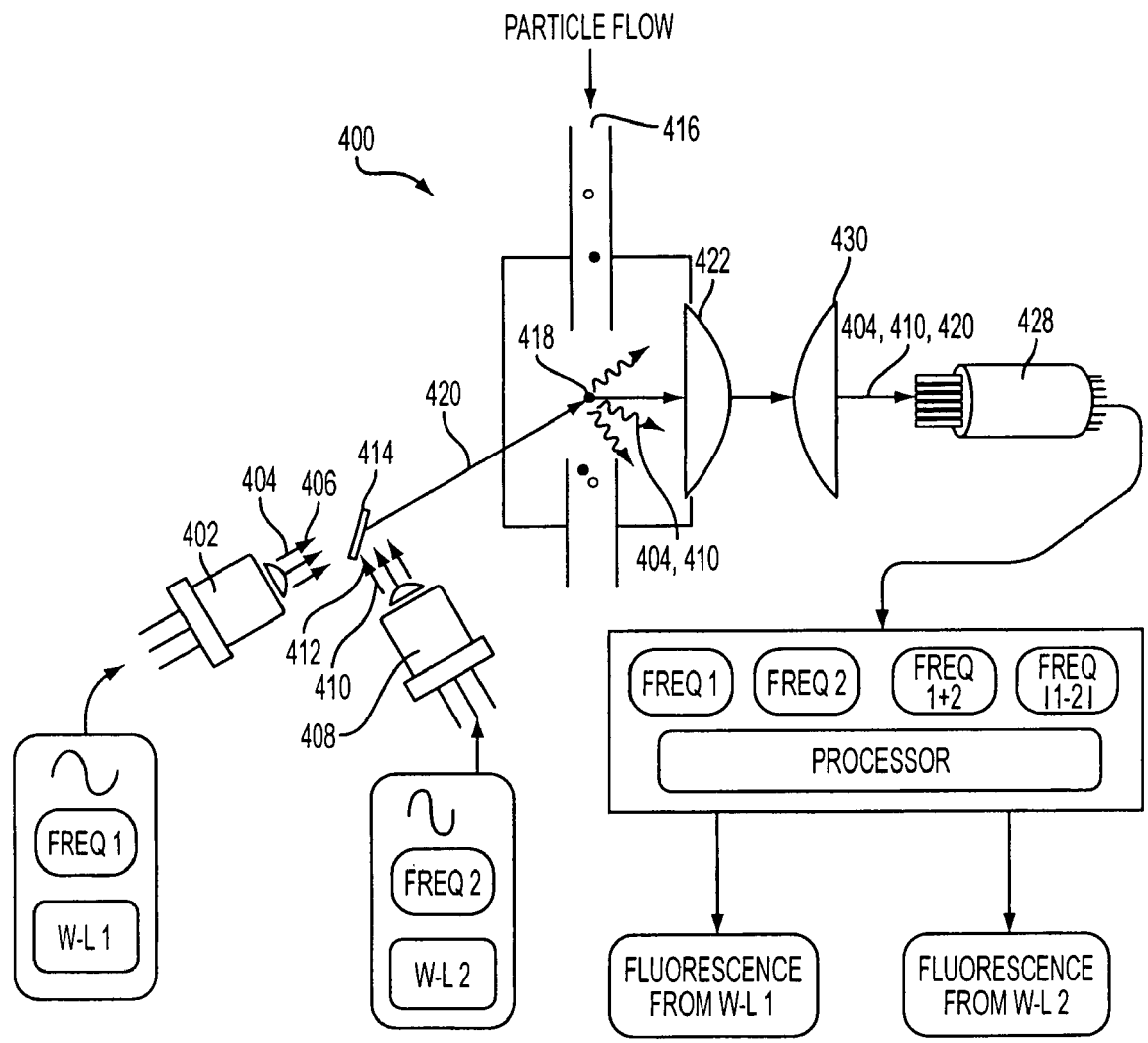
FIG. 4 is a schematic of a system according to a fourth embodiment of the invention.

FIG. 4 is a schematic of a multi-spectral aerosol particle measurement system 400 according to a fourth embodiment of the invention. As shown in FIG. 4, multi-spectral aerosol particle measurement system 400 may include a long emitter 402 emitting in a first direction 406 long wavelength radiation 404 (e.g., light having a wavelength of about 340 nm) and a short emitter 408 emitting in a second direction 412 short wavelength radiation 410 (e.g., light having a wavelength of about 280 nm).

An emitter reflector 414 may be placed at an intersection of first direction 406 and second direction 412 to pass long wavelength radiation 404 in first direction 406 and reflect short wavelength radiation 410 in first direction 406. Emitter reflector may be the same as reflector 314 or 124.

A flowing fluid 416 containing particles (e.g., particle 418) may intersect first direction 406. Radiation 404 or radiation 410 may strike particle 418, causing particle 418 to produce fluorescent wavelength radiation 420. A collimating lens 422 may be positioned to receive and collimate fluorescent radiation 420, as well as scattered long and short wavelength radiation 404, 410.

A focusing lens 430 may be positioned to receive and focus collimated long and short and fluorescent radiation 420. A detector 428 may be positioned at a focus of focusing lens 430 to receive long and short wavelength radiation 404, 410 and fluorescent radiation 420. In one embodiment, detector 428 may be a photomultiplier tube.

In several embodiments, collimating lens 422 and focusing lens 430 may be reflective or refractive optics (e.g., spherical, ellipsoidal, or parabolic reflectors). In several embodiments, an optical fiber or a light pipe may be used to transmit long and short wavelength radiation 404 and 410 to particle stream 416.

In this embodiment, both long emitter 402 and short emitter 408 illuminate particles in fluid 416 with long wavelength radiation 404 and short wavelength radiation 410, respectively. In one embodiment, long emitter 402 and short emitter 408 are modulated at different frequencies.

In this embodiment, long wavelength radiation 404 and short wavelength radiation 410 scatter may be distinguished from fluorescent radiation 420 at detector 428 by analyzing the frequency components of emitted radiation at detector 428. In one embodiment, the modulation frequencies may be significantly higher than the reciprocal of a transit time of particle 418 through long wavelength radiation 404 and short wavelength radiation 410, and may be in the range of 1 to 100 MHz.

In one embodiment, the contribution to the signal produced by detector 428 due to long emitter 402 and short emitter 408 are determined. In this embodiment, the spectral power of the signal at detector 428 could be analyzed at each of the modulation frequencies.

As illustrated in FIG. 4, two or more excitation wavelengths may be superimposed on each other, and each source modulated at different frequency (e.g., in the 1 KHz to 1 GHz range), with each frequency providing 10 or more cycles during the transit time of a particle through the region of space in which the particle is illuminated by the excitation wavelengths. A portion of the inelastic and elastic scatter signals are transmitted by reflective or refractive optics to a detector through a filter or combination of filters that selects the spectra of interest (and may selectively reduce the intensity of the some wavelengths to allow all selected wavelength signals to be detected within the useful linear response region of the detector). The detector output is then a combination of frequencies determined by the modulation frequencies of each source. The optical emission wavelength region determined by the filter or filter combination and corresponding to each source is then determined by Fourier or other electronic spectral analysis, such as frequency down-mixing.

Figure 5:
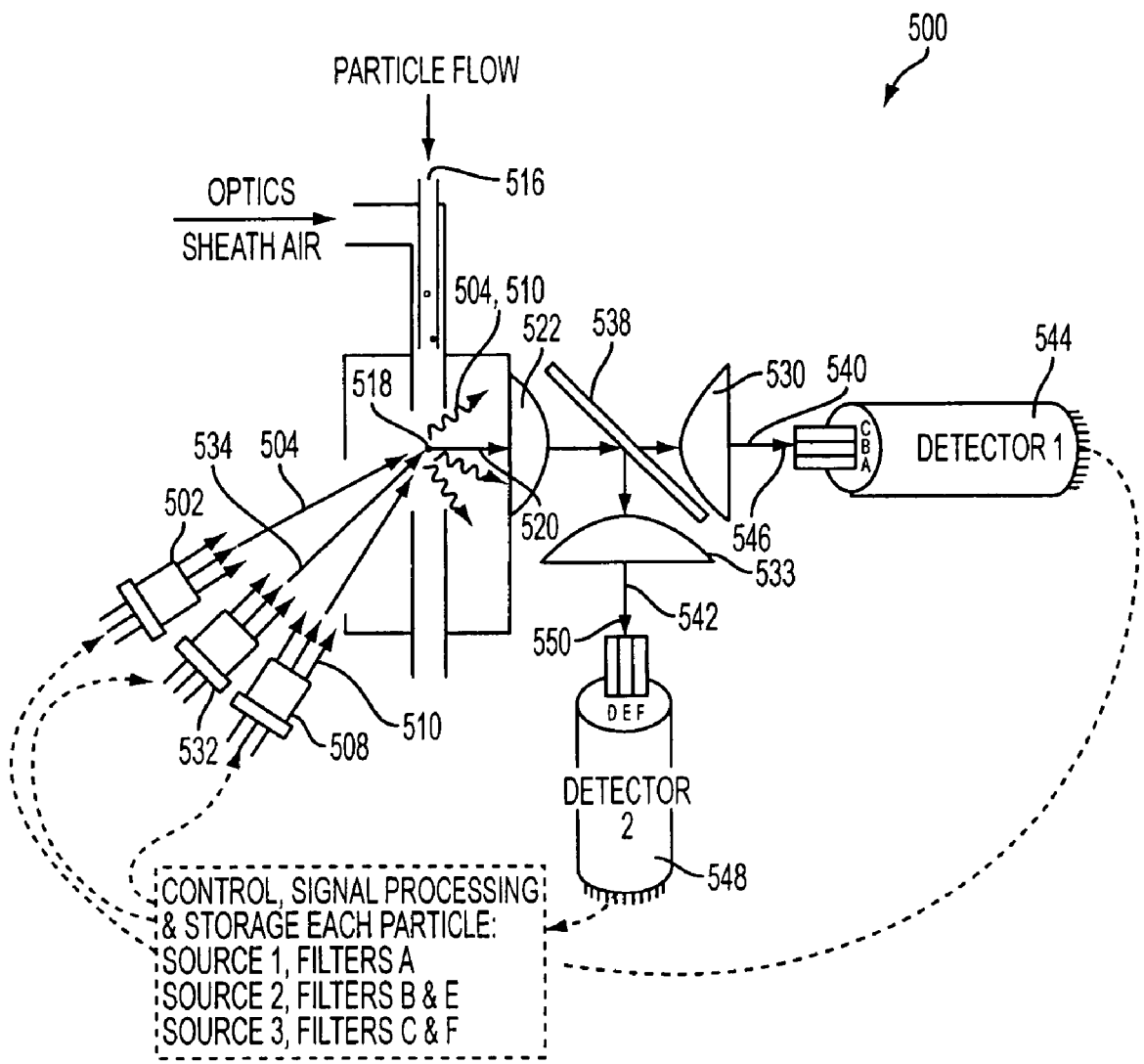
FIG. 5 is a schematic of a system according to a fifth embodiment of the invention.

FIG. 5 is a schematic of a multi-spectral aerosol particle measurement system 500 according to a fifth embodiment of the invention. As shown in FIG. 5, multi-spectral aerosol particle measurement system 500 may include a long emitter 502 emitting long wavelength radiation 504 (e.g., light at approximately 680 nm), a medium emitter 532 emitting medium wavelength radiation 534 (e.g., light at approximately 340 nm), and a short emitter 508 emitting short wavelength radiation 510 (e.g., light at approximately 280 nm).

In this embodiment, a particle 518 in a flowing fluid 516 is exposed to each of first, second, and third excitation wavelengths 504, 510 and 534 at different times because the excitation wavelengths are spatially separated. For example, as shown in FIG. 5, particle 518 is first exposed to excitation radiation 504, and then exposed to excitation radiation 534, and then exposed to excitation radiation 510. When particle 518 is exposed to excitation radiation, the particle may produce fluorescent radiation 520. A portion of the excitation radiation 504, 534, 510 may be scattered by particle 518 as well. A collimating lens 522 may be positioned to receive and collimate the elastic wavelengths (e.g., the scatter) and the inelastic wavelengths (e.g., fluorescent radiation 520).

A filter 538 (e.g., a dichroic filter or other filter) may be positioned to receive and reflect a first portion 540 of fluorescent radiation 520 and transmit a second portion 542 of fluorescent radiation 520. Additionally, filter 538 may also reflect a portion of the elastic radiation. Filter 538 may thus separate scattered long, medium, and short radiation 504, 534, 510 and fluorescent radiation 520 according to a threshold of wavelength.

A first focusing lens 530 may be positioned to receive and focus collimated first portion 540 of fluorescent radiation 520. A first detector 544 is positioned to receive the focused first portion 540 of fluorescent radiation 520. In one embodiment, first detector 544 is a photomultiplier with filters A, B, and C positioned in front of an input of detector 544.

In some embodiments, because excitation radiation 504, 510 and 534 is spatially separated in the region traversed by fluid 516, a particle in fluid 516 (e.g., particle 518) is sequentially exposed to the excitation radiations (e.g., particle 518 is first exposed to radiation 504, then radiation 534, then radiation 510). Preferably, filters A-C are disposed such that when particle 518 is exposed to excitation radiation 504, the elastic and inelastic radiation (or portion thereof) that is produced as a result of the exposure passes through filter-A only prior to reaching detector 544. Similarly, when particle 518 is exposed to excitation radiation 534, the elastic and inelastic radiation (or portion thereof) that is produced as a result of the exposure passes through only filter-B prior to reaching detector 544. Likewise, when particle 518 is exposed to excitation radiation 510, the elastic and inelastic radiation (or portion thereof) that is produced as a result of the exposure passes through only filter-C prior to reaching detector 544. In this way, the fluorescence intensity produced as a result of each excitation wavelength 504, 534 and 510 can be determined according to timing or sequence of signals output from detector 544.

A second focusing lens 533 may receive and focus collimated long, medium, and short wavelength radiation 504, 534, and 510 and second portion 542 of fluorescent radiation 520. A second detector 548 at second focus 550 may receive long, medium and short wavelength radiation 504, 534, and 510 and second portion 542 of fluorescent radiation 520. In one embodiment, second detector 548 is a photomultiplier with filters D, E, and F at an input to second detector 548.

In several embodiments, collimating lens 522 and focusing lenses 530 and 533 may be reflective or refractive optics (e.g., spherical, ellipsoidal, or parabolic reflectors). In several embodiments, an optical fiber or a light pipe may be used to transmit long and short wavelength radiation 504 and 510 to particle stream 516. In several embodiments, an optical fiber or a light pipe may be inserted in the collection path either before or after filter 538.

It may be advantageous to detect multiple emissions wavelengths with a single detector 544, even when two or more detectors 544 and 548 are used to detect multiple emissions from each excitation wavelength, since greater specificity can be obtained using multiple excitation and emission wavelengths.

In this embodiment, there are three light sources, long emitter 502, medium emitter 532, and short emitter 508, and one or more photo detectors 544 and 548. In this embodiment, one of long emitter 502, medium emitter 532, and short emitter 508 may be used to measure scattered light. As discussed above, particle 518 in fluid 516 may flow sequentially through long, medium, or short radiation 504, 534, 510.

In one embodiment, filter 538 is a band pass filter. In this embodiment, filter 538 is positioned to transmit selected wavelengths and to reflect other selected wavelengths. In one embodiment, scattered long, medium, or short radiation 504, 534, 510 and fluorescent radiation 520 is matched with various combinations of first and second detectors 544 and 548 and their-filters A, B, C, D, E, and F.

In one embodiment, short emitter 508 and filter A of first detector 544 are used to measure scattered light while second detector 548 is not used. In another embodiment, medium emitter 532 and filter B of first detector 544, as well as filter E of second detector 548 are used. In a third embodiment, long emitter 502 and filter C of first detector 544 is used with filter F of second detector 548.

Figure 6:
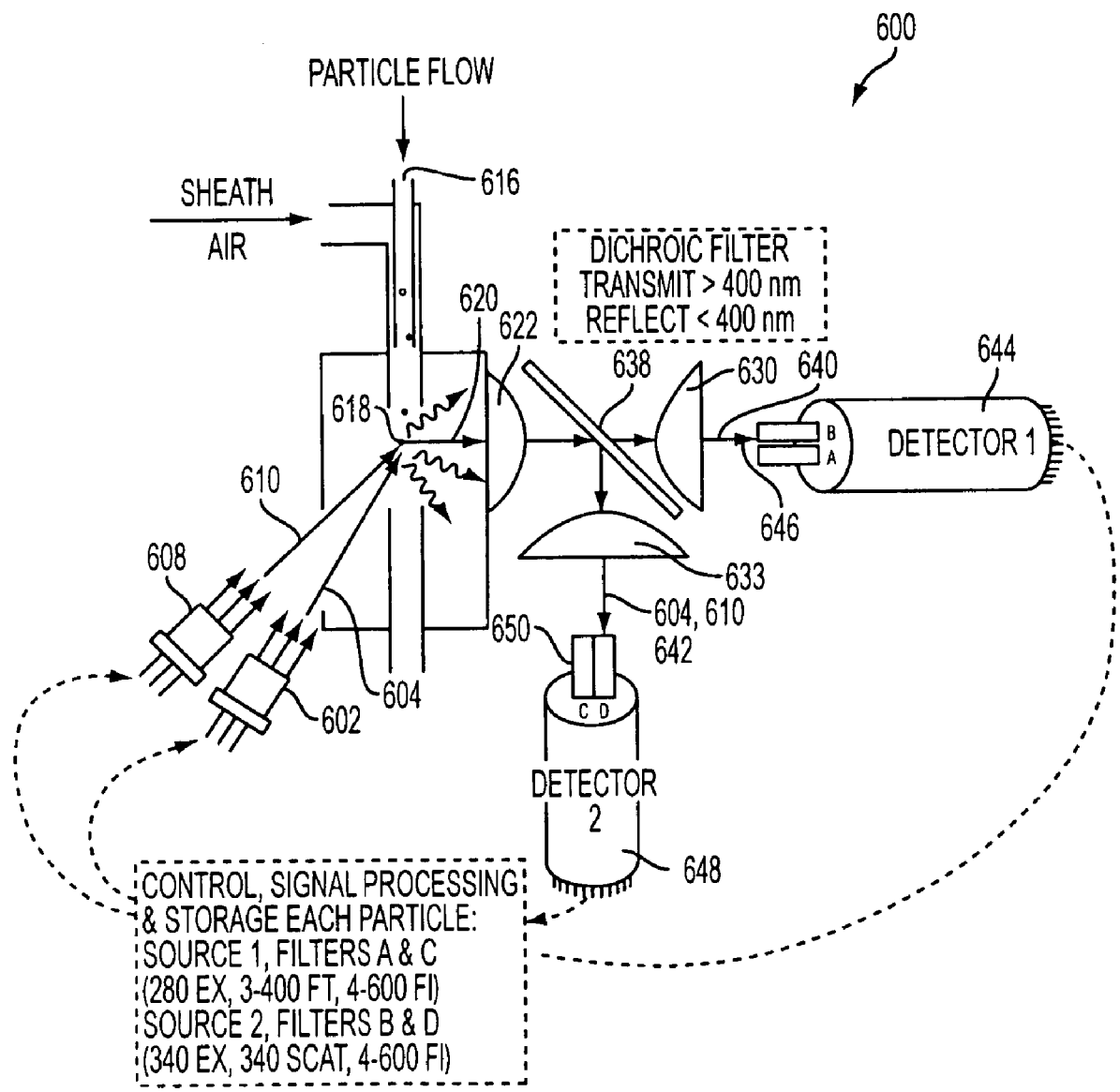
FIG. 6 is a schematic of a system according to a sixth embodiment of the invention.

FIG. 6 is a schematic of a multi-spectral aerosol particle measurement system 600 according to a sixth embodiment of the invention. As shown in FIG. 6, multi-spectral aerosol particle measurement system 600 may include a long emitter 602 emitting long wavelength radiation 604 and a short emitter 608 emitting short wavelength radiation 610.

In this embodiment, a flowing fluid 616 containing particles may intersect each of first and second directions 606 and 612. A particle 618 in fluid 616 intersecting first or second directions 606, 612 may produce fluorescent wavelength radiation 620 when exposed to long or short radiation 604, 610.

A portion of long or short radiation 604, 610 may be scattered by particle 618 as well. A collimating lens 622 may be positioned to receive and collimate scattered long and short radiation 604, 610 and fluorescent radiation 620.

A filter 638 (e.g., a dichroic filter or other filter) may be positioned to receive and reflect collimated long and short radiation 604, 610 and a first portion 642 of fluorescent radiation 620 and transmit a second portion 640 of fluorescent radiation 620. Filter 638 may thus separate scattered long and short radiation 604, 610 and fluorescent radiation 620 according to a threshold of wavelength.

A first focusing lens 633 may be positioned to receive and focus collimated long wavelength radiation 604 and short wavelength radiation 610, and first portion 642 of fluorescent radiation 620. A first detector 648 may be positioned at first focus 650 to receive long wavelength radiation 604 and short wavelength radiation 610, and first portion 642 of fluorescent radiation 620. In one embodiment, first detector 648 is a photomultiplier with filters C and D at an input to first detector 648.

A second focusing lens 630 may be positioned to receive and focus collimated second portion 640 of fluorescent radiation 620. A second detector 644 may be positioned at second focus 646 to receive second portion 640 of fluorescent radiation 620. In one embodiment, second detector 644 is a photomultiplier with filters A and B at an input to second detector 644.

In several embodiments, collimating lens 620 and focusing lenses 630 and 633 may be reflective or refractive optics (e.g., spherical, ellipsoidal, or parabolic reflectors). In several embodiments, an optical fiber or a light pipe may be used to transmit long and short wavelength radiation 604 and 610 to particle stream 616. In several embodiments, an optical fiber or a light pipe may be inserted in the collection path either before or after filter 638.

In one embodiment, long emitter 602 and short emitter 608 are used. In this embodiment, long wavelength radiation 604 from long emitter 602 may be detected at first detector 648 to measure light scatter. In this embodiment, short wavelength radiation 610 from short emitter 608 is detected at second detector 644 to measure fluorescence induced by short wavelength radiation 610.

In an alternative embodiment, long wavelength radiation 604 from emitter 602 may be detected by second detector 644 to measure fluorescence induced by long wavelength radiation 604. In this embodiment, short wavelength radiation 610 from emitter 608 is detected at first detector 648 to measure light scatter.

Figure 7:
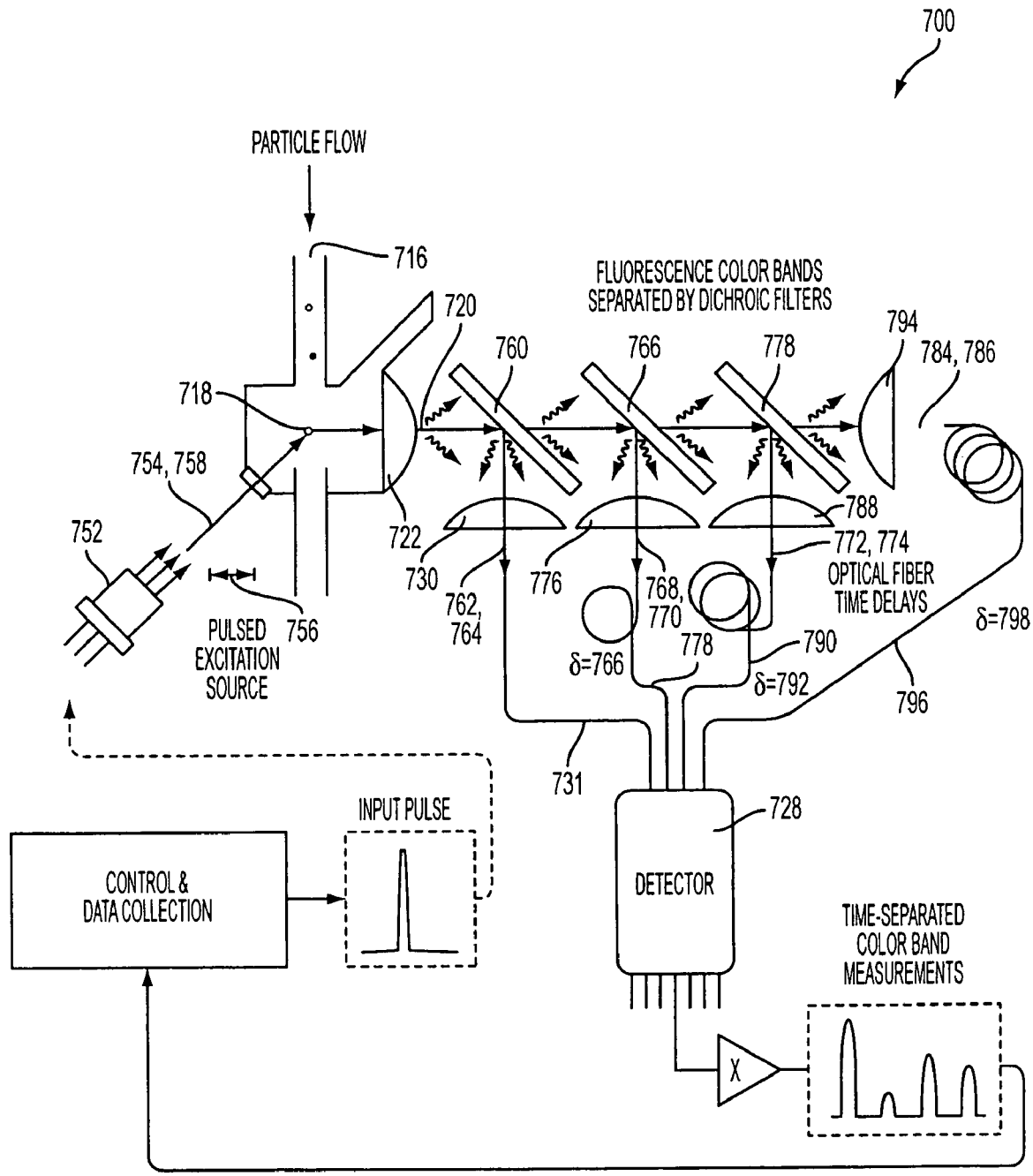
FIG. 7 is a schematic of a system according to a seventh embodiment of the invention.

FIG. 7 is a schematic of a multi-spectral aerosol particle measurement system 700 according to a seventh embodiment of the invention. As shown in FIG. 7, a multi-spectral aerosol particle measurement system 700 may include a pulsed emitter 752 emitting a pulse 754 of radiation for a duration 756 in a direction 758. The radiation output from emitter 752 may have a wavelength in the range of 200-700 nm.

In one embodiment, a fluid flow 716 may intersect direction 758. A particle 718 fluid flow 716 may be exposed to radiation pulse 754 and produce fluorescent radiation 720. Fluorescent radiation 720 may include high, medium and low fluorescent radiation (i.e., fluorescent radiation 720 may include different wavelengths of radiation). Particle 718 may also scatter some of radiation pulse 754. The scattered radiation may include high, medium and low scattered radiation (i.e., the scattered radiation may include different wavelengths of radiation).

A collimating lens 722 may be positioned to receive and collimate the scattered radiation and fluorescent radiation 720. A filter 760 (e.g., a dichroic filter, prism, grating or other filter) may be configured to spatially separate high scattered radiation 762 and high fluorescent radiation 764 from medium and low scattered radiation 768, 772 and medium and low fluorescent radiation 770, 774 according to a threshold of wavelength.

A focusing lens 730 may be positioned to receive and focus only high scattered radiation 762 and high fluorescent radiation 764. An optical fiber 731 (or other transmission path) may be positioned at a focus of focusing lens 730 to receive focused radiation 762 and 764. Optical fiber 731 may transmit radiation 762 and 764 to a detector 728. In one embodiment, detector 728 is a photomultiplier.

A filter 766 may separate medium scattered radiation 768 and medium fluorescent radiation 770 from low scattered radiation 772 and low fluorescent radiation 774 according to a threshold of wavelength. A focusing lens 776 may be positioned to receive and focus only medium scattered radiation 768 and medium fluorescent radiation 770. An optical fiber 778 may be positioned at a focus of focusing lens 776 to receive focused radiation 768, 770. Optical fiber 778 may transmit radiation 768, 770 to detector 728. Radiation 768, 770 may be delayed a period of time 766 by optical fiber 778.

In one embodiment, optical fiber 778 is longer than optical fiber 731. In this embodiment, radiation 768, 770 require a longer period of time to traverse optical fiber 778 than radiation 762, 764 require to traverse optical fiber 731.

A filter 778 may separate low scattered radiation 772 and low fluorescent radiation 774 from residual scattered radiation 784 and residual fluorescent radiation 786 according to a threshold of wavelength. A focusing lens 788 may be positioned to receive and focus only radiation 772, 774. An optical fiber 790 may be placed at a focus of focusing lens 788 to receive focused radiation 772, 774. Optical fiber 790 may delay radiation 772, 774 a period of time 792 and transmit radiation 772, 774 to detector 728.

In one embodiment, optical fiber 790 is longer than optical fiber 778. In this embodiment, radiation 772, 774 require a longer period of time to traverse optical fiber 790 than radiation 768, 770 require to traverse optical fiber 778.

A focusing lens 794 may receive and focus residual radiation 784, 786. An optical fiber 796 may receive focused radiation 784, 786. Optical fiber 796 may delay radiation 784, 786 a period of time 798 and may transmit radiation 784, 786 to detector 728.

In several embodiments, collimating lens 722 and focusing lenses 730, 776, and 788 may be reflective or refractive optics (e.g., spherical, ellipsoidal, or parabolic reflectors). In several embodiments, an optical fiber or a light pipe may be used to transmit pulse 754 to particle stream 716. In several embodiments, an optical fiber or a light pipe may be inserted in the collection path either before or after each high, medium, or low filter 760, 766, and 778.

In one embodiment, pulsed emitter 752 may be a pulsed laser with a pulse duration 756. In this embodiment, duration 756 may be shorter than a transit time of pulse 754 down a practical length of optical fiber.

In on embodiment, pulsed emitter 752 may be used with a particle detection system that includes low-cost visible or near infrared light source. In this embodiment, pulsed emitter 752 is configured so that the generated radiation pulse 754 passes through a predetermined region of space, and the light source in combination with a detector are used to (a) detect when a particle in fluid 716 is within the predefined region or about to enter the region and (b) trigger pulsed emitter 752 to generate a radiation pulse 754 when the particle is detected to be within the predefined region or about to enter the region so that the particle will likely be illuminated by the generated radiation pulse 754.

As discussed above, scattered radiation and fluorescent radiation 720 are separated into high, medium, and low portions 762, 768, 772 and high, medium, and low portions 764, 770, 774, respectively. Each high, medium, and low portions 762, 768, 772 and high, medium, and low portions 764, 770, 774 are focused into separate optical fibers 731, 778, and 790 (or other transmission paths).

Optical fibers 731, 778, and 790 preferably have different optical path lengths. The lengths can be selected so that each of high, medium, and low scattered radiation 762, 768, 772 and high, medium, and low fluorescent radiation 764, 770, 774 are separated in time when arriving at detector 728.

Since each of high, medium, and low portions 762, 768, 772 and high, medium, and low portions 764, 770, 774 arrive separately, the amplitudes of high, medium, and low portions 762, 768, 772 and high, medium, and low portions 764, 770, 774 can be measured individually based on their times of arrival after pulsed emitter 752 emits pulse 754.

For example, if the duration 756 of pulse 754 is 2 nS, which is typical of some pulsed UV lasers, it would be desirable to have 5 to 10 nS elapse between the times separated color bands arrive at detector 728. The time T for pulse 754 to travel down an optical fiber is given by:

$T=L/(c/n)$ where $L$=geometric fiber length, $c$=speed of light in vacuum=$3\times10^8$ m/s, and $n$=refractive index of optical fiber.

Thus, for 10 nS time separation with a fiber refractive index of 1.5, the geometric length of fiber required is 2 meters. Thus in FIG. 7, detector 728 may use optical fiber lengths of 0.1 m for optical fiber 731, 2.1 m for optical fiber 778, 4.1 m for optical fiber 790, and 6.1 m for optical fiber 796.

In one embodiment, an intensity of a first optical signal at detector 728 may be substantially different than that of a second optical signal reaching detector 728. In this embodiment, a dynamic range between first and second optical signals at detector 728 may be too great to cover by conventional signal processing means. Accordingly, an optical density, or transmission, of each of high, medium, and low filters 760, 766, and 778 may be adjusted so that all signal intensities are within a useful range. In addition to (or as an alternative) the following techniques may be used alone or in combination: a gain of detector 728 may be switched rapidly to accommodate the varying incoming radiation; detector 728 may be switched rapidly between predetermined voltages on a photomultiplier dynode chain; detector 728 may be switched rapidly between cathode-to-dynode voltages; detector 728 may be switched rapidly between individual dynode-to-dynode voltages; detector 728 may be an avalanche photo detector in which a bias voltage is changed; detector 728 may use logarithmic amplification; an incoming optical signal may be processed on multiple channels at once.

Another useful method for characterizing threat particles relates to techniques for the analysis of data from a number of particles in order to determine when a target for recognition, such as a bio-aerosol threat, is present. In several embodiments, a variety of pattern classification and recognition methods may be applied to the problem of identifying targets within background particles, such as correlation, principal component analysis, support vector machines, wavelet transforms and multi-dimensional Fourier transforms, and other data mining and pattern recognition methods as may be found in literature.

In one embodiment, particles are measured for a fixed time interval, and the accumulated particle measurements for each time interval are analyzed for the potential presence of threat particles. For each data interval, the degree of pattern match, or the percentage of particles in a target region in data space relative to particles in non-target data space, are tracked versus time and alarm decisions are based on statistically significant increases in the degree of pattern match or percentage.

Since the concentration of background particles and potential threat particles may vary over many (5-6) orders of magnitude, this means that at times of low particle concentration there is relatively large variability in the analysis due to counting statistical variations, while at times of high concentration there are many more particles than are needed for good analysis.

In one embodiment, analysis of the particle stream is performed at variable time intervals but at fixed particle count intervals. In this embodiment, sufficient particle counts may be obtained to make a valid determination of the presence of a biological threat at low particle concentrations. In this embodiment, a determination of the presence of a biological threat may also be made in the shortest possible period while particle concentrations are high Further, many analysis methods require normalization of the particle data. In this embodiment, sampling for a fixed number of particle counts may eliminate the normalization step.

In another embodiment, the data signature of threat or targeted particle is predetermined. In this embodiment, particles can be sampled until a statistically valid number of such predetermined target particle measurements are acquired. This provides for a fast response while assuring that statistical validity is obtained for the decision of whether the target is present.

The methods described above may be performed with continuous wave (CW) excitation sources or pulsed excitations sources. For example, in the systems shown in FIGS. 2, 5 and 6, the excitation source(s) may be CW excitation sources or pulsed excitations sources. When pulsed sources are used, they may be pulsed or turned on during the particle transit through the location of that source, based on timing from prior sensing of the particle, such as from an illumination from an energy source and detection of the scattered energy. The determination of transit may be based either measurement of particle velocity, or on maintaining a controlled flow velocity of the aerosol such that the transit time from the prior sensing to the excitation is known. Use of dichroic filters to combine sources is also an option.

As particles pass individually through one or more excitation sources, the wavelength(s) of a filter or filters may be changed at a rate slower than the transit time of an individual particle, such that a series of particles are sensed each detection wavelength or combination of wavelengths. (For example, individual particles could be sensed for n seconds at filter waveband or waveband combination 1, form m seconds and filter waveband or waveband combination 2, etc.) In this way, over the time period of a release of particles of interest for detection, a subset of particles will be measured with each filter waveband of interest.

Methods for changing filters may include: mechanical repositioning of fixed bandpass filters, tunable gratings, prisms, etalons, and liquid crystal tunable filter, micro-machined tunable gratings, etc.

While various embodiments/variations of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. In a detector system comprising a first emitter, a second emitter, and a detector, a detection method, comprising:

using the first emitter to emit into a region of space first radiation having a first wavelength;

while using the first emitter to emit into the region the first radiation, using the second emitter to emit into the region second radiation having a second wavelength, so that, when a particle transits through the region of space, the particle is simultaneously exposed to the first and second radiation and, in response to being exposed to the radiation, produces elastic and/or inelastic radiation;

modulating the intensity of the first radiation at a first frequency and modulating the intensity of the second radiation at a second frequency, wherein first and second frequencies are different frequencies;

transmitting, by reflective or refractive optics, the elastic and inelastic radiation to the detector through a filter or a combination of filters;

receiving an output signal from the detector; and determining the intensity of said produced elastic radiation that can attributed to the first emitter, the intensity of said produced elastic radiation that can attributed to the second emitter, and the intensity of said inelastic radiation, by analyzing the frequency components of the output signal.

2. The detection method of claim 1, wherein the first emitter and the second emitter are continuous mode emitters, and wherein the output signal generated during the transit time of the particle through the region of space contains at least 10 cycles of each modulating frequency.

3. The detection method of claim 2, further comprising the step of, in response to detecting the particle is within said region of space or about to enter said region of space, causing each of the two emitters to emit said first and second radiation, respectively, while the particle transits through the region.

4. The detection method of claim 3, wherein the step of detecting that the particle is within said region of space or about to enter said region of space comprises using a light source to detect the particle.

5. The detection method of claim 3, wherein the first emitter is configured to emit radiation in a first direction, the second emitter is configured to emit radiation in a second direction that intersects the first direction, and an emitter reflector is disposed at the intersection of the first direction and the second direction, wherein the emitter reflector is configured to pass the first radiation in the first direction and reflect the second radiation in the first direction.

6. The detection method of claim 5, wherein the determining step comprises using Fourier analysis.

7. The detection method of claim 5, wherein the determining step comprises using frequency down-mixing.

8. A detector system comprising:

a first intensity-modulated emitter configured to emit intensity-modulated first radiation modulated at a first frequency into a region of space;

a second intensity-modulated emitter configured to emit intensity-modulated second radiation modulated at a second frequency into the region of space, such that, when a particle transits through the region of space, the particle is simultaneously exposed to the radiation from the first and second emitters and, in response to being exposed to the radiation, produces elastic and/or inelastic radiation, wherein the second frequency is different from the first frequency;

a detector;

reflective or refractive optics configured to transmit the elastic and/or inelastic radiation to the detector;

a processor configured to determine by spectral analysis the intensity of said produced elastic radiation that can attributed to the first radiation, the intensity of said produced elastic radiation that can attributed to the second radiation, and the intensity of said inelastic radiation.

9. The detector system of claim 8, wherein the first emitter and the second emitter are continuous mode emitters.

10. The detector system of claim 9, further comprising a particle detector system for producing a signal when the particle is within said region of space or about to enter said region of space, wherein said signal is configured to cause each of the two emitters to emit said first and second radiation, respectively, while the particle transits through the region.

11. The detector system of claim 10, wherein the particle detector system comprises a light source and a light detector.

12. The detector system of claim 8, wherein the first emitter is configured to emit radiation in a first direction, the second emitter is configured to emit radiation in a second direction that intersects the first direction, an emitter reflector is disposed at the intersection of the first direction and the second direction, wherein the emitter reflector is configured to pass the first radiation in the first direction and reflect the second radiation in the first direction.

13. The detector system of claim 8, wherein the processor is configured to use Fourier analysis to determine the intensity of said produced elastic and/or inelastic radiation that can attributed to the first radiation and the intensity of said produced elastic and/or inelastic radiation that can attributed to the second radiation.

14. The detector system of claim 8, wherein the processor is configured to use frequency down-mixing to determine the intensity of said produced elastic and/or inelastic radiation that can attributed to the first radiation and the intensity of said produced elastic and/or inelastic radiation that can attributed to the second radiation.

15. The detector system of claim 8, further comprising means for modulating the first emitter at a first frequency and means for modulating the second emitter at a second frequency, wherein the output signal generated during the transit time of the particle through the region of space contains at least 10 cycles of each modulating frequency.

16. The detection method of claim 1, wherein the filter or the combination of filters selectively reduce the intensity of some wavelengths to allow all selected wavelength signals to be detected within a useful linear response region of the detector.

17. The detection method of claim 1, wherein the frequency of said produced elastic radiation that can attributed to the first emitter is distinct from said produced elastic radiation that can attributed to the second emitter.

18. The detector system of claim 8, wherein the reflective or refractive optics transmit the elastic and/or inelastic radiation to the detector through a filter or a combination of filters that selectively reduce the intensity of some wavelengths to allow all selected wavelength signals to be detected within a useful linear response region of the detector.

19. The detection method of claim 8, wherein the frequency of said produced elastic radiation that can attributed to the first emitter is distinct from said produced elastic radiation that can attributed to the second emitter.

* * * * *

UNITED STATES PATENT AND TRADEMARK OFFICE
CERTIFICATE OF CORRECTION

PATENT NO. : 7,576,844 B2
APPLICATION NO. : 11/349340
DATED : August 18, 2009
INVENTOR(S) : Hairston et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 152 days.

Signed and Sealed this

Seventh Day of September, 2010

David J. Kappos
*Director of the United States Patent and Trademark Office*